United States Patent [19]

Alt

[11] Patent Number: 5,709,676

[45] Date of Patent: Jan. 20, 1998

[54] SYNERGISTIC TREATMENT OF STENOSED BLOOD VESSELS USING SHOCK WAVES AND DISSOLVING MEDICATION

[76] Inventor: Eckhard Alt, Eichendorffstrasse 52, Ottobrunn, Germany, 85521

[21] Appl. No.: 561,831

[22] Filed: Nov. 27, 1995

Related U.S. Application Data

[63] Continuation-in-part of Ser. No. 270,786, Jul. 5, 1994, abandoned, which is a continuation-in-part of Ser. No. 480,044, Feb. 14, 1990, abandoned.

[51] Int. Cl.$^6$ ............................................. A61N 5/06
[52] U.S. Cl. ..................... 606/7; 606/2; 606/10; 606/15; 604/20; 604/22
[58] Field of Search ............... 606/2–19; 604/20, 604/22

[56] References Cited

U.S. PATENT DOCUMENTS

| | | | |
|---|---|---|---|
| 4,448,188 | 5/1984 | Loeb | 606/7 |
| 4,939,336 | 7/1990 | Meyer et al. | 606/2.5 |
| 4,960,108 | 10/1990 | Reichel et al. | 606/3 |

FOREIGN PATENT DOCUMENTS

| | | | |
|---|---|---|---|
| 8807841 | 10/1988 | WIPO | 606/7 |

Primary Examiner—David M. Shay

[57] ABSTRACT

A method for removing a thrombus or plaque deposit from the wall of a blood vessel of a patient is enhanced by synergistic action of two individual procedures. A catheter is introduced into a blood vessel from which a thrombus or plaque deposit is to be removed. The first procedure is application of laser energy through an optical fiber in the catheter, in a wavelength range selected for preferred absorption by red blood cells in the blood vessel to generate a plasma-based ultrasonic shock wave in the vessel. The shock wave impacts on the thrombus or plaque deposit to open fissures therein. In the second procedure, a thrombus- or plaque-dissolving medication is injected into the blood stream in the vicinity of the plaque deposit through a lumen in the catheter, promptly after completion of the first procedure. The thrombus- or plaque-dissolving medication is used to penetrate into the fissures created in the thrombus or plaque deposit by the shock wave, to begin to break up or dissolve the thrombus or plaque of the deposit. Thereafter, the first and second procedures are repeated in the same sequence at least once, and preferably several times, to ultimately fragment the plaque deposit so that the fragments may be removed from the blood vessel through the channel in the catheter. The overall process, including several repetitions of the sequence of procedures, is carried out in about 10 minutes.

28 Claims, 2 Drawing Sheets

SYNERGISTIC TREATMENT OF STENOSED BLOOD VESSELS USING SHOCK WAVES AND DISSOLVING MEDICATION

CROSS REFERENCE TO RELATED APPLICATION

This application is a continuation-in-part of application Ser. No. 08/270,786, filed Jul. 5, 1994, now abandoned, which is a continuation-in-part of application Ser. No. 07/480,044, filed Feb. 14, 1990, now abandoned, both of which are in the name of the applicant herein, and for which priority is claimed as to common subject matter.

BACKGROUND OF THE INVENTION

The present invention relates generally to treatment of blood vessels to eliminate or reduce deposits attributable to arteriosclerotic processes, and more particularly to the use of ultrasonic pressure waves or shock waves, combined in a unique way with the use of a dissolving medication, for such treatment.

It is known to provide treatment for removal of plaque deposits such as kidney stones by inserting wires into the body to or very near the site of the deposits and then mechanically vibrating the wires at ultrasonic frequencies by use of crystal or magnetostrictive generators located external to the patient's body. Treatment of human atherosclerotic plaque with such method, and with drills, hot tips, and laser radiation, is described in an article by R. J. Siegel et al., entitled "Ultrasonic Plaque Ablation" in *Circulation*, vol. 78. no. 6, Dec. 1988, pp. 1443–1448, where it was stated that various injuries were encountered with the treatment, including vascular perforation. The technique was found to be insufficiently selective to attack the diseased tissue in contrast to healthy tissue.

More recently, Furomoto described in PCT/US86/00886 an approach in which a more selective treatment of yellow colored plaque in the arteries is performed using a laser having a wavelength of 504 millimeters (mm), with a frequency that may lad to higher absorption of energy in the plaque sought to be attacked than in the whiter colored normal, healthy tissue of the arterial wall. Furomoto's approach as described involves direct interaction of laser energy with the arterial wall at the treatment site.

In another article of interest, entitled "Acoustic and Plasma-Guided Laser angioplasty," in *Lasers in Surgery and Medicine*, 9:117 (1989), K. M. Bhatta et al. describe application of laser energy of the aforementioned wavelength to selectively treat diseased portions of a blood vessel, which, however, requires direct contact of the laser fiber with the vessel wall at the treatment site. The effect of the laser energy may be monitored through an analysis of plasma and acoustic signals generated within the vessel wall which are not found with direct application of energy to a normal healthy tissue wall.

In "Laser Arterial Recanalization: A Current Perspective", *Journal of the American College of Cardiology, (JACC)*, vol. 12, no. 1, July 1988, pp. 103–5, G. S. Abela discusses absorption of laser energy by plaque, with conversion thereof to heat to vaporize the plaque. Bare fiber optic delivery systems were found to cause perforation of the artery wall. Attempts to overcome this problem included hot tip and shielded catheters and systems for optical feedback, without success. In "Development and Experimental Application of Contact Probe Catheter for Laser Angioplasty," *JACC*, vol. 9, no. 1, Jan 1987, pp. 101–7, H. Geschwind et al discuss hot tip sapphire contact probe lasers, which operate at relatively low temperatures for evaporation of protein, but require temperatures in excess of 1,800° C. to remove calcified arteriosclerotic lesions.

Other articles of moderate interest regarding use of lasers in angioplasty include B. Keough et al, "Blood Embolization with Hot-Tip?," *First German Symposium on Laser Angioplasty (Proceedings)*, 1988, pp. 236–43; D. Choy, "History of Lasers in Angioplasty," in the same Proceedings, at pp. 56–64; J. Isner et al, "Cardiovascular Laser Therapy: The Optimal Laser," in the same Proceedings, at pp 65–9; and B. Verdaasdonk et al, "Comparison of Hot Tip and Sapphire Tip Recanalization," in the same Proceedings, at pp. 70–80. B. Harnoss et al, in the same Proceedings at pp 147–56, presented an article entitled "Experience in Excimer Laser Photoablation of Arteriosclerotic Plaques," where the procedure showed moderate success with soft tissue but little with plaque, the tissue removal again being non-selective between diseased and healthy tissue and creating a serious risk of vessel wall perforation.

Other techniques for removal of clots, thrombi, and plaque from blood vessel walls include rotary cutters and scrapers, which are particularly risky in cases of seeking calcified plaque removal. Balloon angioplasty is also ineffective for removal or compression of calcified lesions. Use of stents to reinforce and maintain the vessel open serve no purpose for removal of thrombus or plaque.

Sonic shock waves have been used successfully for fragmenting small stones in the urinary tract, and laser induced shock wave lithotripsy has been used to treat bladder stones and stones in the urinary tract without thermal effects. See, for example, R. Hoffman et al, "Laser Induced Shock Wave Lithotripsy-Biologic Effects of Nanosecond Pulses," *Journal of Urology* 139: 1077–79, 1988; "Use of Pulsed Nd:YAG Laser in the Ureter," *Urologic Clinics of North America*, vol. 15, no. 3, Aug 1988, pp. 369–75; and "First Clinical Experience with a Q-Switched NeoDymium:YAG Laser for Urinary Caliculi," *Journal of Urology* 141:275–9, 1989. In these cases, treatment was restricted to highly calcified urologic stones, not for arteriosclerotically diseased human vascular tissue.

1987 statistics reported in *Bild der Wissenschaft*, April 1989, indicated that 205,000 bypass operations and 260,000 balloon dilatations—angioplasty—of coronary arteries. About 50% of the bypass patients reoccluded, and almost 75% of the angioplasty patients. But in hindsight, these results may have been predictable because bypass involves surgical procedures with substantial change in the vascular flow pattern leading to accelerated growth of new arteriosclerotic lesions, and angioplasty only compresses the fatty deposits with resultant trauma to the vessel.

It is evident, then, that despite considerable attention having been given to treatment of arteriosclerotically affected blood vessels with selective removal of thrombi and plaque, truly satisfactory procedures for achieving those ends without serious risk to the patient have not heretofore been available. In particular, the procedures proposed to date have had either no success or the ability to remove some portions of the deposits with high risk of vessel wall perforation or reocclusion.

It is a principal aim of the present invention to provide improved methods of treating arteriosclerotically affected blood vessels in a way that will relatively rapidly remove virtually the entirety of the deposit whether of soft tissue or calcified material, without significant likelihood of injury to healthy tissue, with particular avoidance of vessel wall perforation.

It is a related object of the invention to provide a treatment regimen that enables highly selective as well as rapid removal of diseased material from the vessel wall to unblock the vessel and return to near normal blood flow.

SUMMARY OF THE INVENTION

According to the invention, a method is provided for removing deposits of thrombus or plaque from the wall of a blood vessel of a patient by synergistic action of two individual procedures, after introduction of a catheter into a blood vessel from which such a deposit is to be removed. The first procedure is to deliver laser energy of predetermined wavelength range through an optical fiber in the catheter. The predetermined wavelength range is selected for preferred absorption by red blood cells in the blood vessel to generate a plasma-based ultrasonic shock wave in the vessel for application to the deposit to create openings, fissures, or cracks in the deposit. The second procedure is to deliver a preselected deposit-dissolving medication into the blood stream in the vicinity of the deposit through a channel or lumen in the catheter promptly after completion of the first procedure. The deposit-dissolving medication penetrates into openings created in the deposit by the shock wave to begin to break it up or dissolve it. Thereafter, the first and second procedures are repeated in the same sequence at least once, and preferably several times, to ultimately fragment the deposit so that the fragments may be removed through the channel in the catheter.

The step of repeating the first and second procedures is performed without substantial interruption following completion of performance of an initial sequence of the first and second procedures. In essence, the first procedure is performed over a time interval of about two minutes, and the second procedure is then performed over a time interval of about another two minutes. The first and second procedures are repeatedly performed in that sequence for an overall duration of at least about ten minutes.

The deposit-dissolving medication used in the second procedure is preferably selected from among urokinase, streptokinase, and rTPA, in a dosage selected to restrict the action of the medication to substantially only the locality of the deposit to avoid systemic action of the medication throughout the patient's vascular system.

Therefore, it is another important object of the invention to provide methods of treating stenosed blood vessels by taking advantage of the synergistic effect of two individual procedures, one of which applies laser/plasma-induced shock waves to the site of the stenosis to achieve breakup of the stenosis material without injury to adjacent healthy tissue, and the other of which applies a thrombus- or plaque-dissolving medication to the site of the stenosis in a dosage selected to produce only local, rather than systemic, effect in the vascular system.

BRIEF DESCRIPTION OF THE DRAWINGS

The above and still further aims, objects features, aspects, and attendant advantages of the invention will become clear from a description of a presently preferred embodiment and method thereof, constituting the presently contemplated best mode of practicing the invention, especially when taken in conjunction with the accompanying drawings, in which.

DETAILED DESCRIPTION OF THE PREFERRED EMBODIMENT AND METHOD

Common subject matter is disclosed in the applicant's co-pending application Ser. No. 08/270,786, filed Jul. 5, 1994, of which the present application is a continuation-in-part. The '786 application is itself a continuation-in-part of application Ser. No. 07/480,044, filed Feb. 14, 1990. The specifications of both of the earlier applications are incorporated herein by reference.

Figure 1:
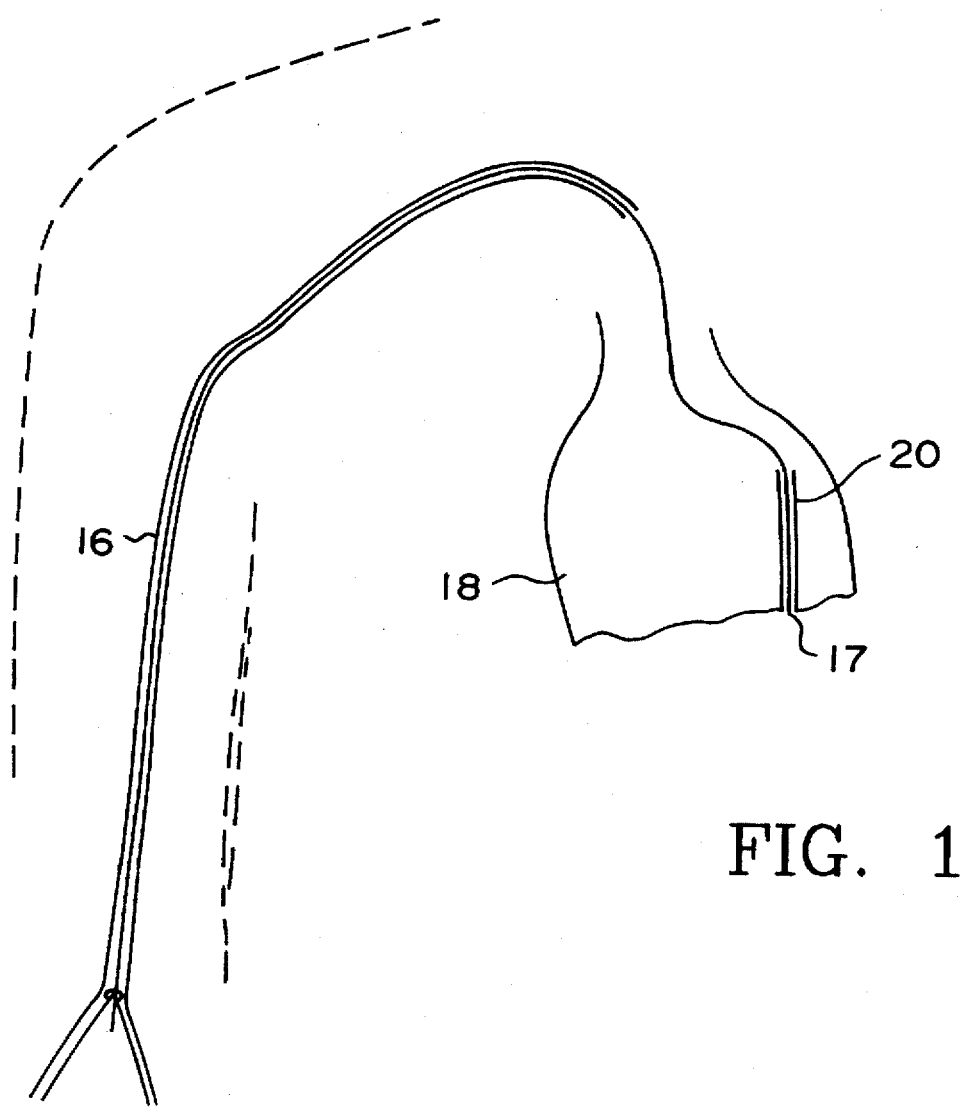
FIG. 1 is a partial phantom view of a patient with a catheter inserted into the vascular system to treat blood vessels such as the coronary arteries.

Referring to FIG. 1, a flexible catheter 15 is inserted into the vascular system of a human patient such as by means of a blood vessel 16 in the arm or groin of the patient. The catheter includes an optical fiber 17 running the length thereof and exposed at the distal end for delivering laser energy into a blood vessel from which a deposit of plaque or thrombus is to be removed, such as a coronary artery 20 on the patient's heart 18. Preferably, the distal end of the catheter is disposed in the vicinity of the deposit to be removed, and laser energy is transmitted from a laser generator, to be discussed presently, coupled to the optical fiber at the proximal end of catheter 15 at a point external to the patient's body.

Figure 2:
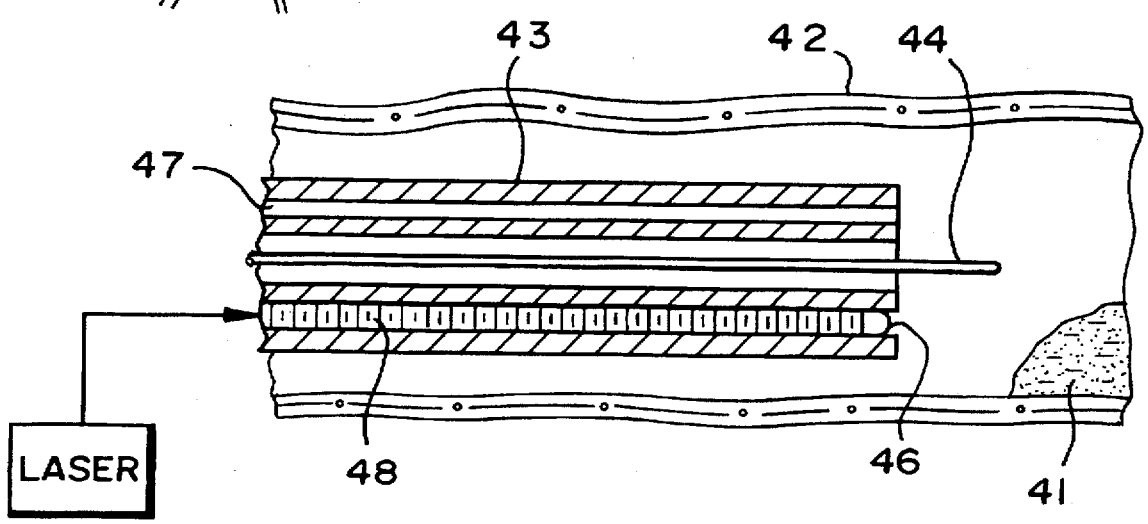
FIG. 2 is a magnified view of partial section of a coronary artery illustrating a site of an occlusion or stenosis of the vessel, and showing the positioning of the distal end of a catheter therein or administering the two treatment procedures.

As represented by the simplified cross-section view of FIG. 2, a deposit 41 which may be plaque, or thrombus, or stenosis of other type, formed in the blood vessel 42 and remaining attached to the internal surface of the vessel is to be removed from the vessel wall by the method of the present invention. The distal end of catheter 43 is positioned in the vessel to facilitate two individual procedures which have a synergistic effect on the break-up of the deposit 41 and removal of debris therefrom from the blood vessel itself. To that end, the catheter has a central lumen running from the proximal end to the distal end thereof to accommodate a guide wire 44 on which the catheter is readily advanced or withdrawn through the vascular system of the patient to and from the treatment site of interest, which in this example is in the vicinity of deposit 41. Additionally, the catheter has two other lumens running its full length, one of which is to accommodate the optical fiber or fiber bundle 48 by which laser energy is delivered to the region of the treatment site within the vessel 42, and the other lumen 47 being open to allow fluid to be passed therethrough.

Figure 3A:
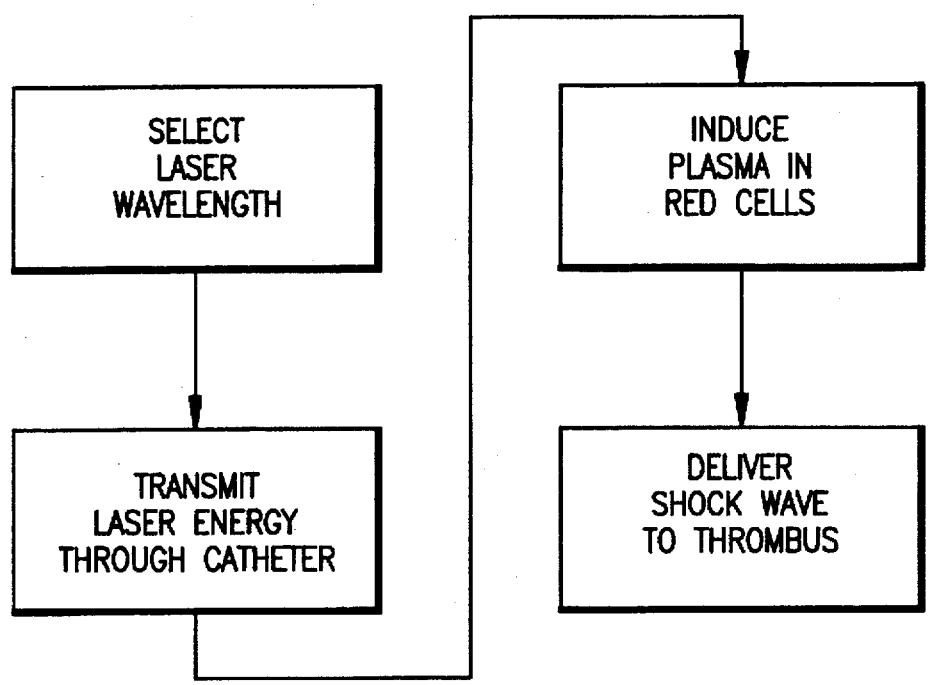
FIGS. 3A and 3B are respectively flow diagrams of the two procedures which are applied sequentially and sequenced repetitively, according to the invention.
Figure 3B:
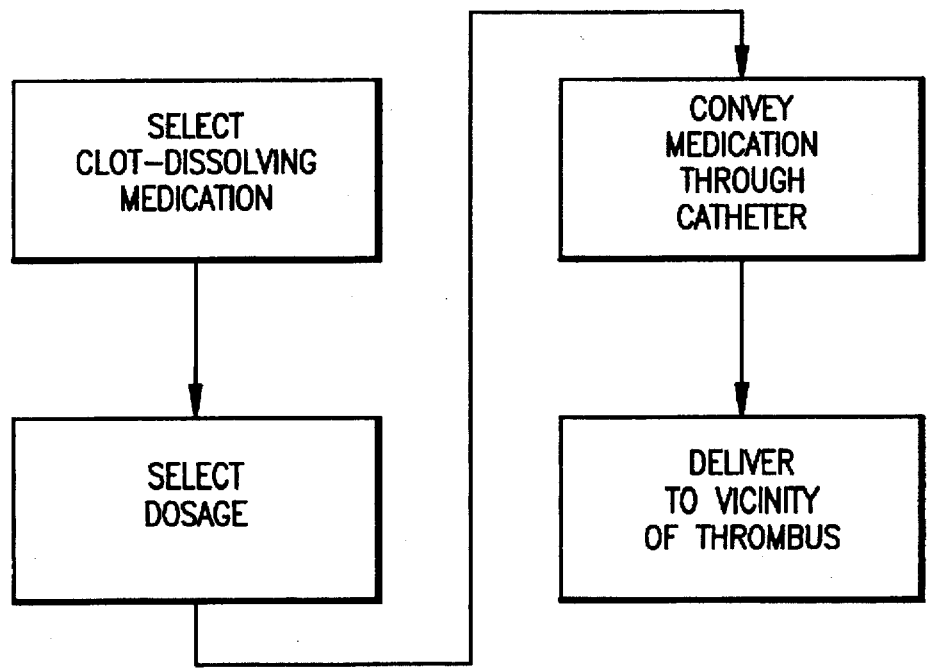

Referring now to FIGS. 3A and 3B, the two procedures which are performed to remove deposit 41 from the blood vessel, include a first procedure in which laser energy is transmitted via the optical fiber (or bundle) 48 into the blood vessel at a wavelength in a predetermined range for preferred absorption by red blood cells of the deposit, such as in the appropriate portion of the range between 250 and 1064 nanometers (nm). Optical fiber diameters in the range from 100 to 250 microns are suitable, and pulse durations of the laser energy may be at 100 microseconds or longer. The delivery of the laser energy of about 60 microjoule (mj) pulses at a wavelength or wavelengths in the red portion of the spectrum produces an interaction between the laser energy and the blood to create a plasma in the red blood cells. No plasma will be created in other colors, because the red color of the blood cells is so highly absorbent to the selected frequency (reciprocal of wavelength) of the laser light as to create a plasma there only.

This is important, because if the laser beam is applied to the vessel wall, which is wide, the energy absorption is not as great as the energy concentration to create a plasma in this way. Moreover, if the laser energy were not made selective in this manner, it could result in perforation of the vessel wall which has tended to plague the efforts at laser use for removing deposits in the past. The effect of this procedure is to induce a plasma-based ultrasonic shock wave which impacts on the stenosis or deposit to be removed, to creates fissures, cracks, or openings therein, as well as to partially fragment the material into particles.

A beneficial combination of the procedure by which shock waves are induced with a procedure by which the material to be removed is partially softened and dissolved, is attained by a second procedure implemented without substantial interruption following completion of the first. The second procedure is to deliver a clot-dissolving medication, such as streptokinase, urokinase, or rTPA, through the open channel 47 of the catheter. It is important that the dosage of the deposit-dissolving medication be selected to produce only a local effect—that is, in the vicinity of the deposit—and in all events less than that dosage which is capable of producing a systemic thrombolytic effect. For streptokinase, the dosage for producing a local effect only is in the range from about 5,000 to about 10,000 units; for urokinase, from about 6,000 to about 10,000 units; and for rTPA, from about one milligram (mg) to about five mgs.

Investigations conducted by or for the applicant herein have demonstrated that if a clot is treated with laser light alone, for example, using the principles of the present invention for inducing the shock waves, partial dissolution would occur over time by breaking up the clot in response to the shock waves. If the clot is treated by applying only a clot-dissolving medication, such as streptokinase or other suitable agent, a very slow loss of thrombus weight takes place indicative of some dissolution of the thrombus. If, however, the two techniques are combined, a more rapid process of reduction takes place. For example, some 40% of the weight of the thrombus may be dissolved after ten minutes,—of which about 35% would be attributable to the laser energy and the remaining 5% to the clot-dissolving medication. Further progress in reduction of the deposit occurs considerable more slowly.

But if, as taught by the present invention, the aforementioned first and second procedures are performed sequentially, and the sequence is performed repetitively, a synergistic effect is achieved which not only significantly improves on performing either procedure alone, but also substantially betters the results achieved with a simple combination of the two procedures. So, if the clot is treated with laser light, then the clot-dissolving medication is applied, and then laser light is applied again, followed by applying the clot-dissolving medication again, and then the laser light again, and so forth, in about 1½ or 2 minute steps, and that sequence is repeated several times, a dissolution of 90 to 100% of the clot is achieved within the same time frame as occurs for a combination of the two individual treatments which produce a reduction by weight of only 40% of the deposit, i.e., approximately 10 minutes.

Thus, the effect of treatment according to the present invention is not only an additive effect, but a true synergistic effect which amplifies the action of the two individual procedures alone by combining them in what amounts to short, but repeated bursts. The much enhanced effect is believed to occur as a result of the laser shock waves breaking up the small connections within the clot to allow the clot-dissolving medication to more easily penetrate to sites in the clot at which it can act with much greater efficiency. Normally, if a clot is placed in a streptokinase environment, only the immediate surface layers undergo removal—resulting in only a small percentage—5% or less—of the thrombus weight being dissolved, even in a period of half an hour or more. But by creating cracks or fissures in the thrombus by means of repeated application of laser shock waves interspersed by application of the clot-dissolving medication, then the action of the medication is amplified by allowing it to much more rapidly and efficiently reach and dissolve the entire thrombus.

This same beneficial effect occurs even for an older thrombus that arose, for example, from a previous surgery, such as emboli which may be two or three months old. These, too, can be dissolved completely within a relatively short time interval of about ten minutes on average.

The procedure has major implications on the treatment of patients with thrombus—even with cerebral stroke where it may be assumed that there has been an embolic event. Normally, such patients cannot be treated with clot-dissolving medication alone because of high-risk side effects such as severe bleeding problems following the systemic action of the medication. But since the medication is applied only locally, in dosages of about 10,000 units or less (for urokinase and streptokinase), whereas overall systemic action may require dosages of 1,000,000 to 4,000,000 units, the side effects are minor while the local effect is amplified.

The essence of the invention, then, is that the laser/plasma-induced shock waves reenforce the action of the clot-dissolving medication, and vice versa. Additionally, and significantly, both treatment methods may be applied by means of the same catheter, without need for withdrawal and repositioning. The laser fiber (optical fiber) is disposed within a lumen of the catheter. The catheter itself may have a diameter of about one mm (about 3 French), the laser fiber may be about 200 microns in diameter, with cladding on its surface for protection and restriction of the laser energy to its interior during transmission. A separate channel or lumen is provided in the catheter for introducing the clot-dissolving medication and for withdrawing the dispersed particulate blood clot material (debris). With this small diameter, the catheter is durable and flexible, with a size sufficiently small to traverse even the relatively tiny blood vessels to the patient's brain.

The catheter may be visually steered and placed at a remote site by fluoroscopy. In addition, a dye solution may be applied by injection through the catheter lumen which is otherwise used for application of the clot-dissolving medication, to visualize the degree of thrombus reduction, or, stated somewhat differently, to visualize the restoration of blood flow.

Animal studies performed by the applicant have shown that a thrombus clot induced artificially in an animal, either in a vein or an artery of a pig, for example, and left in place for several days, can be dissolved within ten minutes with the combined action of the laser shock waves and the clot-dissolving medication. The present treatment method is also very much concerned with reducing the tissue damage produced by the laser beam. Since the laser energy is converted to mechanical energy, in accordance with the invention, very little injury occurs to the healthy tissue compared to the extent of harm produced by prior art methods in which laser radiation is applied directly to the thrombus and the vessel wall, thereby creating heat shrinkage and other undesirable side effects which can cause new thrombus formation or even perforation of the vessel wall.

By inducing a shock wave, the energy is readily absorbed without injury, as a result of the elastic structure of the vessel. Moreover, unlike prior art techniques, the blood vessel remains open on a long term basis following treatment according to the invention, based on the animal research conducted using this treatment method.

Although a presently preferred method of treatment has been described herein, various modifications may suggest themselves to persons of ordinary skill in the field of the invention from a consideration of the foregoing detailed description, without departing from the spirit and scope of the invention. It is therefore desired that the present invention shall be limited only by the appended claims, and the rules and principles of applicable law.

What is claimed is:

1. A method of treating clots in a blood vessel of a patient, which comprises the steps of alternately applying, first, laser energy in the vessel to induce a plasma-based shock wave through the blood to impact the clot to create fissures therein, and, then, a clot-dissolving medication in a local, non-systemic manner to the clot; repeating a sequence of shock wave and dissolving medication applications over a period of time sufficient to fragment the clot; and removing fragmented clot material from the patient's bloodstream.

2. The treatment method of claim 1, including applying each of the laser-induced shock wave and the clot-dissolving medication for an interval of about two minutes in a substantially uninterrupted sequence, and repeatedly performing the sequence.

3. The treatment method of claim 1, including applying each of the laser-induced shock wave and the clot-dissolving medication through a single catheter introduced into the blood vessel to a point sufficiently close to a site of the clot to enable said fragmentation of the clot to be achieved by combined and repeated action of said applications.

4. The treatment method of claim 1, including inducing the shock wave by creating a plasma through application of laser energy to the patient's blood adjacent the site of the clot at radiation wavelengths in a predetermined range which is susceptible to high absorption by red blood cells.

5. The treatment method of claim 4, including applying both said laser energy and said clot-dissolving medication through a single catheter introduced into the patient's vascular system from a point external to the body.

6. The treatment method of claim 1, including applying the clot-dissolving medication in each said sequence in a dosage less than capable to produce a systemic thrombolytic effect, to assure only local rather than systemic action thereof in the patient's vascular system.

7. The treatment method of claim 6, wherein the clot-dissolving medication is streptokinase.

8. The treatment method of claim 6, wherein the clot-dissolving medication is urokinase.

9. The treatment method of claim 6, wherein the clot-dissolving medication is rTPA.

10. The treatment method of claim 1, wherein said period of time is at least about ten minutes.

11. A method of eliminating thrombus formations in a blood vessel of a patient, which comprises the steps of successively introducing laser energy in a predetermined wavelength range for preferred absorption by red blood cells of a thrombus in the blood vessel which is to be removed, to generate a plasma-based ultrasonic shock wave in the vessel for application to the thrombus to expose at least a portion of the interior of the thrombus, and promptly thereafter delivering a thrombus-dissolving medication into the blood stream in the region of said thrombus to be removed to penetrate to said exposed portion of the interior of the thrombus; and repeating said successive introduction of laser energy to re-generate said shock wave and said prompt delivery of thrombus-dissolving medication at least once again to fragment a portion of said thrombus, so that the fragmented portion of the thrombus may be removed from the vessel.

12. The method of claim 11, wherein the thrombus-dissolving medication is rTPA.

13. The method of claim 12, including delivering said thrombus-dissolving medication in a dosage of from about 1 to about 5 milligrams, whereby to restrict action thereof to locally in the vicinity of the thrombus rather than systemically.

14. The method of claim 11, wherein the thrombus-dissolving medication is urokinase.

15. The method of claim 14, including delivering said thrombus-dissolving medication in a dosage of from about 6,000 to about 10,000 units, whereby to restrict action thereof to locally in the vicinity of the thrombus rather than systemically.

16. The method of claim 11, wherein the thrombus-dissolving medication is streptokinase.

17. The method of claim 16, including delivering said thrombus-dissolving medication in a dosage of from about 5,000 to about 10,000 units, whereby to restrict action thereof to locally in the vicinity of the thrombus rather than systemically.

18. The method of claim 11, further including removing the fragmented thrombus portion from the vessel.

19. The method of claim 18, including introducing said laser energy and delivering said thrombus-dissolving medication by means of a single catheter threaded into the patient's vascular system and used for both.

20. The method of claim 19, including removing said fragmented thrombus portion from the vessel through said single catheter.

21. The method of claim 11, including generating said shock wave and delivering said thrombus-dissolving medication in successive time intervals of about two minutes each without substantial interruption, and repeating said generating and said delivering successively several times over.

22. The method of claim 21, including introducing said laser energy and delivering said thrombus-dissolving medication successively through a single catheter introduced into the patient's blood vessel at a point sufficiently close to a site of the thrombus to achieve said fragmenting of the thrombus by synergistic action thereof.

23. A method for removing deposits of thrombus or plaque from the wall of a blood vessel of a patient by synergistic action of two individual procedures, which comprises the steps of introducing a catheter into a blood vessel from which such deposit is to be removed; as a first procedure, delivering laser energy of predetermined wavelength range through an optical fiber in said catheter for preferred absorption by red blood cells in said blood vessel to generate a plasma-based ultrasonic shock wave in the vessel for application to said deposit to create openings therein; as a second procedure, delivering a deposit-dissolving medication into the blood stream in the vicinity of said deposit through a channel in said catheter promptly after completion of the first procedure to penetrate into the openings created in said deposit; and repeating said first and second procedures in that sequence at least once to fragment a portion of said deposit.

24. The method of claim 23, further including removing fragments of said deposit from said blood vessel through said channel in said catheter.

25. The method of claim 23, wherein the step of repeating said first and second procedures is performed without substantial interruption following completion of performance of an initial sequence of said first and second procedures.

26. The method of claim 25, including performing said first procedure over a time interval of about two minutes, and then performing said second procedure over a time interval of about another two minutes.

27. The method of claim 26, including repeatedly performing said first and second procedures in said sequence for an overall duration of at least about ten minutes.

28. The method of claim 27, wherein the deposit-dissolving medication used in said second procedure is selected from among urokinase, streptokinase, and rTPA, in a dosage selected to restrict the action of said medication to substantially only the locality of said plaque deposit to avoid systemic action of said medication throughout the patient's vascular system.

* * * * *